United States Patent [19]

Spencer

[11] 4,438,778

[45] Mar. 27, 1984

[54] MAXIMUM PRESSURE SELECTOR DEVICE

[75] Inventor: William R. Spencer, Springdale, Ohio

[73] Assignee: General Electric Company, Cincinnati, Ohio

[21] Appl. No.: 317,107

[22] Filed: Nov. 2, 1981

[51] Int. Cl.$^3$ .............................................. F16K 11/06
[52] U.S. Cl. ..................................... 137/112; 277/165
[58] Field of Search ................. 137/112, 113; 277/165

[56] References Cited

U.S. PATENT DOCUMENTS

| | | | |
|---|---|---|---|
| 1,675,231 | 6/1928 | Stoke | 137/112 |
| 2,057,286 | 10/1936 | Ash | 141/9 |
| 2,311,851 | 2/1943 | McClure | 137/113 |
| 2,440,478 | 4/1948 | Kehle | 137/113 |
| 2,501,755 | 3/1950 | Bent | 137/113 |
| 2,509,672 | 5/1950 | Christensen | 277/165 |
| 2,627,388 | 2/1953 | Johnson et al. | 251/118 |
| 3,033,578 | 5/1962 | Kellogg | 277/165 X |
| 3,633,606 | 1/1972 | Hay | 137/113 |
| 3,972,343 | 8/1976 | Burge | 137/112 |
| 4,018,244 | 4/1977 | Burns | 137/113 |

Primary Examiner—Robert G. Nilson
Attorney, Agent, or Firm—Gregory A. Welte; Derek P. Lawrence

[57] ABSTRACT

A maximum pressure selector device in which a valve ball is pressure actuatable in a chamber intermediate two cooperating valve seats of opposing input chambers. Positioned between the seats is a pair of orifices which connect the intermediate chamber to an output port. The orifices are of a predetermined size for allowing a predetermined maximum fluid flow rate therethrough for reducing surge flow. The valve ball is positioned in an encircling sealing arrangement centrally located in the intermediate chamber and is restricted to limited movement therein. The input chambers communicate with the intermediate chamber and thus with the output port, depending on the seating position of the valving element.

15 Claims, 2 Drawing Figures

INPUT SIGNAL PRESSURE    OUTPUT SIGNAL PRESSURE    INPUT SIGNAL PRESSURE

MAXIMUM PRESSURE SELECTOR DEVICE

The present invention relates to a maximum pressure selector device and more particularly to a new and improved means for surge flow control.

BACKGROUND OF THE INVENTION

In surge flow systems it is desirable to provide means whereby an output port can be isolated from an input port in order to control the flow of fluids in a system. This flow control has heretofore been achieved through the use of a maximum pressure selector device.

Typically, maximum pressure selector devices have been constructed to comprise a valve ball enclosed in a chamber and located between two opposing input ports. The application of a higher pressure signal at either of the ends of the chamber drives the ball to the opposite seat and thereby cuts off the resulting lower pressure signal from the other input port. This valve action controls flow through an intermediately disposed output port.

In typical maximum pressure selector devices, the mid-position force on the ball is relatively small enabling the ball to be jammed by dirt accumulating in the space between the valve ball and the chamber wall. Excessive surge flow problems resulting from such jamming can disturb the operation of critical devices operating from a common regulated supply pressure. Additionally, some prior art devices have not been as quickly responsive to control pressures as desired for certain applications.

SUMMARY OF THE INVENTION

In one form of the invention, I provide a maximum pressure selector device comprising a chamber and a spaced pair of inlet ports communicating with the chamber. A spaced pair of valve seats is disposed between the inlet ports. An outlet port is disposed between the valve seats and includes a pair of spaced orifices communicating with the chamber. At least one of the orifices is of a predetermined cross-sectional area for allowing a predetermined maximum fluid flow rate therethrough for reducing surge flow between the inlet ports. A valving element is disposed between the valve seats and is pressure actuatable toward alternate ones of the valve seats. The valving element has a stroke less than the distance between the orifices. Sealing means is positioned in the chamber about the valving element and is in sealing engagement therewith throughout the stroke thereof.

DESCRIPTION OF THE PREFERRED EMBODIMENT

Figure 1:
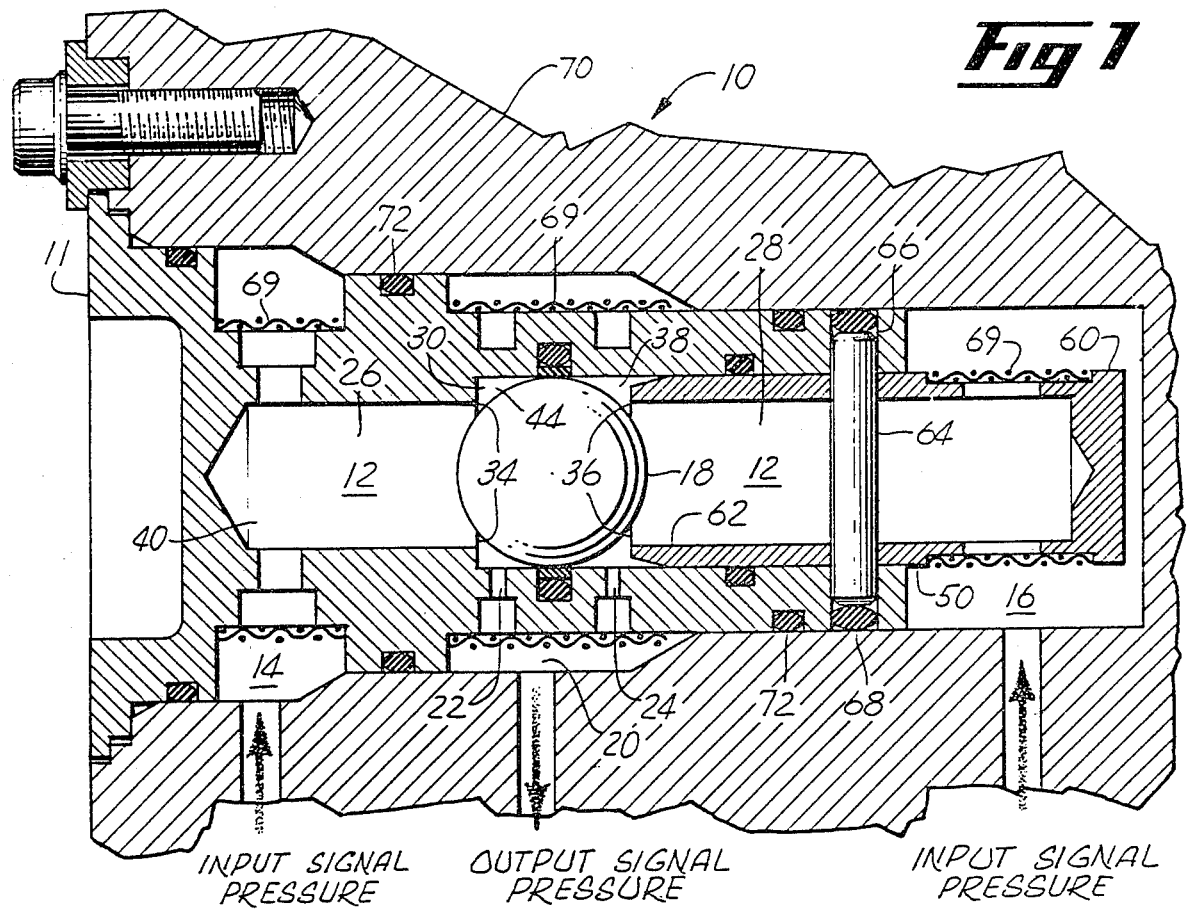
FIG. 1 is a longitudinal cross-sectional view of one form of the maximum pressure selector device of the present invention.

As illustrated in FIG. 1, in one form of the invention, the maximum pressure selector device 10 comprises a body member 11 containing a cylindrical chamber 12 having a longitudinally spaced pair of inlet ports 14 and 16 which communicate with chamber 12. Restrained for limited movement within chamber 12 between the inlet ports 14 and 16 is a valving element which advantageously is a valve ball 18 but which can have any suitable configuration such as that of a solid cylinder. An outlet port 20 comprises a pair of longitudinally and predeterminedly spaced orifices 22 and 24 which also communicate with chamber 12. Orifices 22 and 24 are located on opposite sides of the central-most position of valve ball 18, and jointly establish the only output means from chamber 12 to other potential systems that may be connected to outlet port 20. As will be understood more fully later, at least one of the orifices is of a predetermined cross-sectional area, e.g., 0.001 sq. in., for allowing in a predetermined acceptable maximum fluid flow rate therethrough so as to reduce surge flow between the input ports 14 and 16. Preferably, both of the orifices 22, 24 are of the selected cross-sectional area.

Cylindrical chamber 12 comprises a pair of longitudinally spaced cylindrical sections 26 and 28. These sections 26 and 28 define the space in which fluids circulate during operation of the device 10. An intermediate cylindrical section 30 is disposed between sections 26 and 28 and is of a greater diameter than that of sections 26 and 28. The valve ball 18 is captured in and its movement, or normal stroke, is limited by the outer ends of the intermediate cylindrical section 30; and the orifices 22 and 24 are disposed on opposite sides of the valve ball 18 throughout the stroke thereof. More particularly, at the junctions of the several cooperating sections of the chamber 12, annular valve seats 34 and 36 are defined. Between seats 34 and 36 is located a cylindrically shaped space 38 in which the ball 18 is retained. As the ball moves in either direction, its motion will be halted either by seat 34 on one side or seat 36 on the other.

Valve ball 18 has a diameter which is predetermined in relation to the longitudinal spacing of the valve seats 34 and 36 for determining the operating stroke of the ball. It should be noted that this invention encompasses the diversity to use different ball sizes dependent upon the application with which it is put to use.

In operation, fluids enter the device 10 at respectively different pressures through inlet ports 14 and 16. These fluids then communicate with the pair of longitudinally spaced sections 26 and 28 of the chamber 12. Pressure differentials between the fluids cause ball 18 to move in the direction in which the pressure of the fluid exerted on the ball is greater. For example, if the pressure of the fluid at inlet port 14 is greater than that at inlet port 16, the force exerted on ball 18 will be greater than the force impeding the movement created by the fluid from inlet port 16. Consequently, ball 18 will move to the right in the drawing until it comes to rest against seat 36. Conversely, if the pressure of the fluid from inlet 16 is greater than that of inlet port 14, the ball will move to the left and come to rest against seat 34.

Thus, valve ball 18 is alternatively engageable with one or the other of the valve seats 34 or 36 depending upon the fluid pressure differential thereacross. While ball 18 is in transition from one seat to the other, there is a flowpath open from the then high pressure input port to the then low pressure input port by way of the orifices 22, 24. However, the orifices 22, 24 are in series thereby limiting this transient flow from the high to the low pressure area in chamber 12. In addition, as noted previously, the orifices 22, 24 are provided with cross-sectional areas which allow a predetermined maximum fluid flow rate therethrough which would be acceptable for the involved application of the device 10. For example, for a typical application, a maximum fluid flow rate may be approximately one cubic inch per second.

Fluid outlet port 20 communicates with intermediate section 30 through the pair of output orifices 22 and 24 connected to the intermediate section. Each orifice is located on one side of the central-most position of valve ball 18 and immediately adjacent a respective valve seat. As a result of this arrangement, whenever ball 18 is substantially centrally located within space 38 there will be a direct path for fluids to flow from sections 26 and 28 through both orifices 22 and 24, and then exit the device through outlet port 20.

Longitudinally spaced section 26 is defined by a cylindrical bore 40 in body member 11. Likewise, intermediate section 30 is defined by counterbore 44 in body member 11. As illustrated in FIG. 1, the diameter of counterbore 44 is larger than that of bore 40. As a consequence, seat 34 is created at the point where the bore 40 ends and the counterbore 44 begins. The remaining spaced section 38 is further defined by tubular plug 50 which is secured in counterbore 44. A more detailed description is provided hereinbelow.

Figure 2:
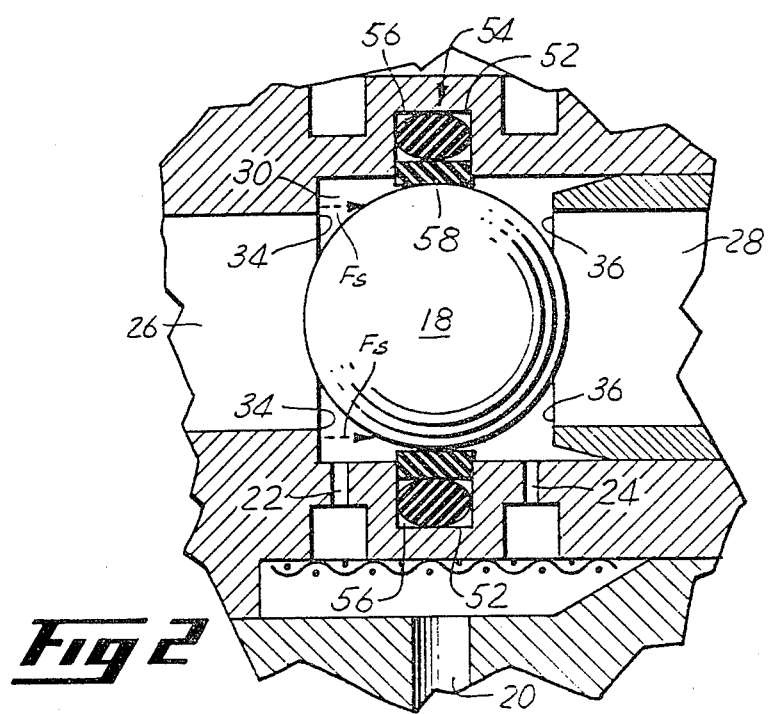
FIG. 2 is an enlarged fragmentary cross-sectional view of the valving element, the valve seat and the sealing assembly features of the device of FIG. 1.

As seen in FIG. 2, cylindrical intermediate section 30 includes an annular groove 52. Annular groove 52 is centrally positioned between the pair of seats 34 and 36. Groove 52 contains an annular sealing arrangement 54, comprising an O-ring 56 and sealing member 58. The sealing member 58 comprises a resilient, relatively low friction material, for example, a tetrafluoro ethylene fluorocarbon polymer, such as the one available under the trademark Teflon, having ball 18 sealingly positioned therein throughout the operating stroke of the ball. That is, the stroke or distance in which ball 18 is allowed to move is limited to the extent that ball 18 is always in contact with annular sealing arrangement 54. As shown in FIG. 2, annular sealing arrangement 54 may comprise a resilient, e.g., elastomeric, O-ring 56 which is disposed in the outer periphery of the annular groove 52 and a sealing member 58 which is disposed in the inner periphery of the groove 52. Thus, ball 18 will always remain in contact with sealing member 58 during its normal stroke, including ball positions against seat 34 or against seat 36.

The combination of sealing member 58, O-ring 56, sets 34 and 36, ball 18 and orifices 22 and 24 provides a snap action in driving the ball 18. More specifically, as the ball lifts off the then high pressure seat, additional force on the ball is created as the then high pressure section 26 or 28 cooperates with increased surface area of the ball 18. For example, in the situation in which section 26 is at relatively higher pressure than section 28, the additional snap force is shown as arrows Fs in phantom in FIG. 2. This is a regenerative action i.e., the additional force increases as the ball moves off the high pressure seat, and thus gives the ball the snap-acting characteristic. For example, the mid-position force for 0.50 inch diameter ball and a 215 psi pressure differential is about 42 pounds. Under these conditions, with the ball on the high pressure seat, the force available to move the ball is about 21 pounds.

The purpose of O-ring 56 and sealing member 58 in combination is two-fold. First, the combination prevents transient fluid flow around ball 18. This particular aspect is achieved from the ball 18 being in physical contact with sealing member 58 throughout its stroke. Secondly, the combination creates a sufficiently tight fit between the ball and annular sealing member 58 which also serves toward reducing any accumulation of dirt and other debris therebetween and thereby reduces the mentioned tendency toward jamming of the ball in mid-position by such dirt and debris.

It is to be appreciated that in the device 10, a very high mid-position force is exerted on the ball 18 to drive it to the proper seat. This is in contrast to typical maximum pressure selection devices in which the mid-position force can be relatively small and the ball is subject to jamming by dirt in the clearance between the ball and the wall of the ball chamber. Further, in the device 10, the only flowpath from the high pressure input signal to the low pressure input signal, while the ball is in transit, is through the two orifices 22, 24 in series. This limits surge flow through the device to a tolerable level. Hence, excessive surge flow will not tend to disturb critical control devices operating from a same regulated supply pressure.

Referring again to FIG. 1, tubular plug 50 more specifically can comprise a removable member 60 which has an inner end 62 defining valve seat 36. Furthermore, inlet port 16 is provided in plug 50. Plug 50 can be separately formed and is inserted into body member 11. These components cooperate with one another to comprise the maximum pressure selector device 10.

Plug 50 can be fixedly secured in the body member 11 through the use of locking pin 64. Locking pin 64 extends radially through the body member 11. This is achieved by inserting the pin into aligned apertures in plug 50 and body member 11. Inasmuch as this insertion technique is radial in nature the pin 64 will actually extend through the entire diameter of body member 11. The pin can also easily be removed in order to disassemble the device whenever necessary. Locking pin 64 is secured in place by O-ring 68. O-ring 68 is elastomeric and is tightly fitted around plug 50 in an annular groove 66 and thus is effective for retaining the pin 64.

The maximum pressure selector device 10 can effectively handle liquids of diverse characteristics and thus filter means can be provided to prevent large-sized metal clips or other foreign objects from clogging the system. This can be provided through the use of screen elements 69 which are included at all points of input of the maximum pressure selector device 10. Although the screen elements are disclosed as one possible example of filter means, it is to be understood that any other suitable filter arrangement can be used.

In order to ensure fluid integrity, body member 11 is sealingly positioned in casing 70. Generally, body member 11 is totally contained within casing 70, having inlet and outlet ports which communicate with respective ones of the inlet and outlet ports in the body member.

It will be clear to persons skilled in the art that in devices of the type described wherein plug 50 is fitted into body member 11 a juncture is created therein causing potential for leakage between the inlet and outlet ports 14, 16 and 20. O-ring seals 72 seated in appropriately located annular grooves, e.g., in the body member 11, are provided to prevent such occurrences. Through use of such O-rings, fluids are deterred from flowing to the exterior of the device as well as between different pressure points and thusly the integrity of the maximum pressure selector device is maintained.

Although the maximum pressure selector device of the present invention has been described as preferably including two orifices of predetermined cross-sectional area, it is to be recognized that only one orifice need be of the predetermined area to accomplish the desired surge flow reduction. Also, although the device of the present invention has been shown with an intermediate cylindrical section of greater diameter than that of the adjacent cooperating sections, if desired, the intermediate section may be of a smaller diameter than the cooperating sections as long as appropriate structure is provided to serve as the required valve seats.

After reference to the foregoing, modifications of this invention may occur to those skilled in the art. However, it is to be understood that this invention is not intended to be limited to the particular embodiments shown and described herein, but is intended to cover all modifications coming within the spirit and scope of the invention as claimed.

I claim:

1. A maximum pressure selector device comprising:
   (a) a chamber;
   (b) a spaced pair of inlet ports communicating with said chamber;
   (c) a spaced pair of circular valve seats disposed between said inlet ports;
   (d) an outlet port disposed between said valve seats and comprising a pair of spaced orifices communicating with said chamber, at least one of said orifices being of a predetermined cross-sectional area for allowing a predetermined maximum fluid flow rate therethrough for reducing surge flow between said inlet ports;
   (e) a ball-shaped valving element disposed between said valve seats and being pressure actuatable toward alternate ones of said valve seats and having a stroke less than the distance between said orifices; and
   (f) sealing means comprising a resilient sleeve positioned about said ball positioned in said chamber about said valving element and being in sealing engagement therewith throughout the stroke thereof.

2. The invention of claim 1, wherein said sealing means further comprises an elastomeric O-ring encircling said sleeve and disposed between said sleeve and said wall of said chamber.

3. A maximum pressure selector device comprising:
   (a) a body member including a cylindrical chamber comprising a pair of longitudinally spaced cylindrical sections, an intermediate cylindrical section of larger diameter than that of said pair of sections and cooperating therewith in defining longitudinally spaced circular valve seats;
   (b) a separate fluid inlet port respectivley communicating with each of said pair of longitudinally spaced sections;
   (c) a valve ball positioned in said intermediate section and being pressure actuatable toward alternate ones of said valve seats;
   (d) a fluid outlet port communicating with said intermediate section and comprising a pair of orifices connected to said intermediate section each on one side of the central-most position of said valve ball, at least one of said orifices being of a predetermined cross-sectional area for permitting a maximum fluid flow therethrough for reducing surge flow between said inlet ports; and
   (e) a sealing member fitted in said intermediate section about said ball and of sufficient axial length to maintain sealing engagement therewith throughout the stroke thereof.

4. The invention of claim 3, wherein one of said pair of longitudinally spaced sections is defined by a cylindrical bore in said body member, said intermediate section is defined by a counterbore in said body member, and the other of said longitudinally spaced sections is defined by a tubular member fixedly secured in said counterbore.

5. The invention of claim 4, wherein one of said cylindrical sections comprises a tubular member having an inner end extending a predetermined distance into said counterbore and defining a circular valve seat.

6. The invention of claim 5, wherein said tubular member is fixedly secured in said counterbore by a removable locking pin extending through radially aligned apertures in said tubular member and said body member.

7. The invention of claim 6, wherein said pin is secured in place by an annular member fitted about the body member.

8. The invention of claim 3, wherein said intermediate section includes an annular groove located between said pair of orifices of said fluid outlet and containing said sealing member.

9. The invention of claim 8, wherein said annular sealing arrangement comprises a resilient O-ring seated in the outer periphery of said annular groove and an annular resilient, relatively low friction sealing member positioned in the inner periphery of said groove and greater in width than the operating stroke of said ball.

10. The invention of claim 3, wherein the body member is sealingly positioned in a casing having inlet and outlet channels communicating with respective ones of said inlet and outlet ports in said body member.

11. The invention of claim 3, further comprising O-ring seals deterring fluid flow between said inlet and outlet ports and to the exterior of said device.

12. The invention of claim 3, wherein said valve ball is alternatively engageable with one or the other of said valve seats depending on the fluid pressure differential thereacross, said ball enables substantial fluid flow from one side of said cylindrical chamber to said outlet port through only one of said orifices thereof when said ball engages one of said valve seats, and said ball enables substantial fluid flow from the other side of said cylindrical chamber to said outlet port through only the other one of said orifices when said ball engages the other one of said valve seats.

13. The invention of claim 3, wherein said inlet and outlet ports include filter means.

14. A maximum pressure selector device comprising:
   (a) a body member including a cylindrical chamber comprising a pair of longitudinally spaced cylindrical sections, an intermediate cylindrical section of greater diameter than that of said pair of sections and cooperating therewith in defining longitudinally spaced annular valve seats, one of said pair of longitudinally spaced sections being defined by a cylindrical bore in said body member, said intermediate section being defined by a counterbore in said body member and having an annular groove therein, and the other of said longitudinally spaced sections being defined by a tubular member fixedly secured in said counterbore, said tubular member comprising an inner end defining an annular valve seat, said tubular member being fixedly secured in said bore, said body member being sealingly positioned in a casing having inlet and outlet channels;

(b) a separate fluid inlet port extending from an inlet channel in said casing and communicating with each of said pair of longitudinally spaced sections;
(c) a fluid outlet port extending from an outlet channel in said casing and communicating with said intermediate section and comprising a pair of orifices connecting to said intermediate section each on one side of a central-most position therein and adjacent a respective one of said valve seats;
(d) a valve ball positioned in said intermediate section and being alternatively engageable with one or the other of said valve seats depending on the fluid pressure differential thereacross, said ball enabling substantial fluid flow from one side of said cylindrical chamber to said outlet port through only one of said orifices thereof when said ball engages one of said valve seats, and said ball enabling substantial fluid flow from the other side of said cylindrical chamber to said outlet port through only the other one of said orifices when said ball engages the other one of said valve seats; and
(e) an annular sealing arrangement positioned in said intermediate section about said ball and of sufficient axial length to maintain sealing engagement therewith throughout the stroke thereof, said annular sealing arrangement comprising a resilient O-ring seal seated in the outer periphery of said groove in said intermediate section and a resilient, relatively low friction sealing sleeve seated in said annular groove within said O-ring and about said valve ball and greater in length than the operating stroke of said ball, whereby said ball is actuated with a snap action effective for reducing tendency toward jamming thereof by debris in said chamber.

15. The invention of claim 14, wherein said orifices are of a predetermined cross-sectional area for allowing a predetermined maximum fluid flow rate therethrough for reducing surge flow between the inlet ports.

* * * * *